United States Patent [19]

Mahruki

[11] Patent Number: 4,592,740

[45] Date of Patent: Jun. 3, 1986

[54] VAGINAL SPONGE APPLICATOR

[76] Inventor: Nimetullah M. T. Mahruki, Ortaköy, Palanga cad. Süreyya Bey Apt., Istanbul, Turkey

[21] Appl. No.: 678,062

[22] Filed: Dec. 4, 1984

[51] Int. Cl.⁴ ............................................. A61F 13/20
[52] U.S. Cl. ...................................... 604/15; 128/127
[58] Field of Search ................... 604/15, 11, 16, 17, 604/18, 54, 55, 57, 59, 12, 13, 218; 128/127–131

[56] References Cited

U.S. PATENT DOCUMENTS

| | | | |
|---|---|---|---|
| 1,537,257 | 5/1925 | Mizner | 604/13 |
| 2,351,836 | 6/1944 | Popper | 604/16 |

Primary Examiner—John D. Yasko
Attorney, Agent, or Firm—Evelyn M. Sommer

[57] ABSTRACT

An applicator is provided which is adapted to insert a vaginal sponge into a woman's vagina directly against the cervix. The applicator comprises an outer barrel open at an upper end for receiving and delivering a vaginal sponge against the cervix. Piston means are further provided within the outer barrel and include gripping means at one end thereof external of the barrel and a piston head at the opposite end thereof internal within the barrel. An ejector lever is pivotably mounted on the internally contained piston head and is adapted to deliver the vaginal sponge out of the barrel through the upper open end and directly against the cervix at an angle relative to the applicator as the piston head is caused to travel in the direction of the open upper end of the barrel.

14 Claims, 6 Drawing Figures

VAGINAL SPONGE APPLICATOR

BACKGROUND OF THE INVENTION

The present invention relates generally to a vaginal sponge applicator and, more particularly, to such a vaginal sponge applicator which may be used by an untrained person for the self-application of vaginal sponges.

Devices heretofore used for the insertion of vaginal sponges into the lowermost parts of the human vagina were oftentimes incapable of being self-applied due to the complexity of their structure and the possibility of damage to the vaginal mucosa if improperly used. As such, these devices could only be used by a trained professional. Other, less complex devices which did not present such difficulties, were incapable of being sterilized prior to insertion and, as such, were potential sources of infection.

Against the foregoing background, it is a primary object of the present invention to provide a vaginal sponge applicator for inserting a vaginal sponge into the lowermost part of the human vagina and directly against the cervix.

It is another object of the present invention to provide such an applicator which is relatively simple in structure and which can be used without the assistance of a trained professional.

It is still another object of the present invention to provide such an applicator which will not injure the vaginal mucosa during use.

It is yet another object of the present invention to provide such an application which is able to be sterilized prior to each application.

SUMMARY OF THE INVENTION

To the accomplishments of the foregoing objects and advantages, the present invention, in brief summary, comprises an application adapted to insert a vaginal sponge into a woman's vagina and directly against the cervix. The applicator comprises an outer barrel open at an upper end and adapted to receive a vaginal sponge at the upper end and deliver the sponge directly against the cervix at an angle relative to the applicator. Piston means are further provided within the outer barrel for effecting delivery of the sponge. The piston means include gripping means at one end thereof and external to the barrel and a piston head at the opposite end thereof internal within the barrel. The piston head is adapted to travel within the barrel toward and away from the open upper end. Ejector lever means are pivotably mounted on the internally contained piston head and are adapted to force the vaginal sponge out of the barrel through the upper end as the piston head is caused to travel toward the open upper end. Due to the pivotable action of ejector lever, the sponge is delivered directly against the cervix at an angle relative to the applicator.

BRIEF DESCRIPTION OF THE DRAWINGS

The foregoing and still other objects and advantages of the present invention will be more apparent from the following detailed explanation of the preferred embodiments of the invention in connection with the accompanying drawings, wherein.

DETAILED DESCRIPTION OF THE PREFERRED EMBODIMENTS

Figure 2:
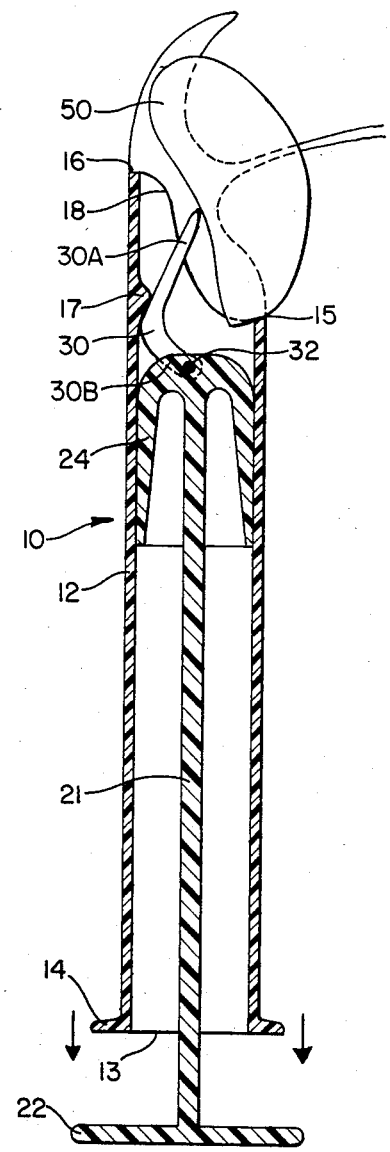
FIG. 2 is a sectional side elevational view of the application as it delivers the vaginal sponge directly against a woman's cervix.

The applicator of the present invention, referred to generally by reference numeral 10, includes an elongated tubular outer barrel 12 which contains a movable piston 20 provided therein. Elongated tubular barrel 12 is open at its opposite upper and lower ends 13A and 13, respectively. A gripping flange 14 is provided about the lower end 13 of the barrel to facilitate gripping by the user during use. The piston 20 is adapted to be inserted into the barrel 12 through the lower end 13 thereof. The upper end 13A of the outer barrel 12 is angled or tapered from an upper edge 16 to a lower edge 15 to facilitate insertion of the upper end 13A of the barrel 12 into the vagina of a woman and to permit the applicator 10 to generally conform to the woman's cervix 50 as shown in FIG. 2. A detent 17 is provided on the interior wall of the barrel 12, preferably positioned below the upper edge 16 and approximately across from the lower edge 15 of the upper end 13A of the barrel. The lower portion of the detent 17 is gradually curved.

Moveable piston 20 includes an elongated shaft 21 having a gripping device 22 provided at one end thereof and a head 24 at its opposte end. The gripping device 22 is located external to the barrel 12 and the piston head 24 is generally located internally within the barrel 12. Gripping device 22 constitutes a T-shaped handle. The head 24 which is provided at the opposite end of the shaft 21 is generally U-shaped with a diameter substantially equal and slightly less than the interior diameter of the barrel 12. The head 24 of the piston 20 is adapted to be travel within the barrel 12 toward and away from the open upper end 13A of the barrel 12 by the force exerted by the user on the gripping device 22 of the piston 20.

Figures 3, 4:
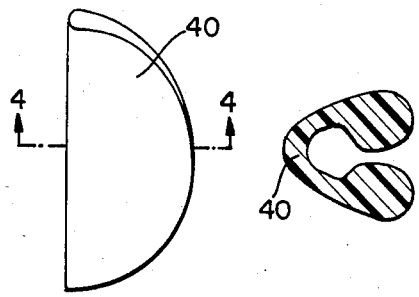
FIG. 3 is a top view of the vaginal sponge in a folded-over position ready for loading into the applicator of FIG. 1.
FIG. 4 is a sectional view taken along line 3—3 of FIG. 3.
Figures 5, 6:
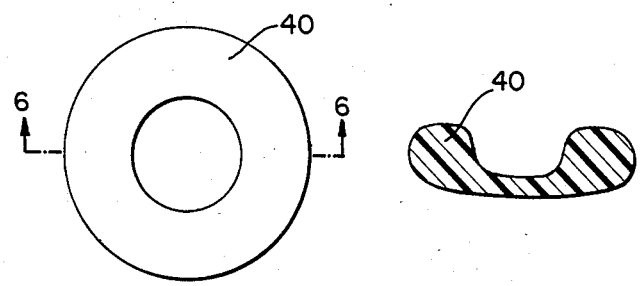
FIG. 5 is a top view of the vaginal sponge in a fully open position.
FIG. 6 is a sectional view taken along line 5—5 of FIG. 5.

A generally circular or disc shaped vaginal sponge 40 is shown in an unfolded top view in FIG. 5 and in a sectional view in FIG. 6. The vaginal sponge 40 is adapted to be folded in half as shown in FIGS. 3 and 4 and is inserted into the upper end 13A of the barrel 20 until it comes into contact generally with the head 24 of the piston 20. As the open upper end 13A of the barrel 12 is tapered or angled, the sponge 40, in a loaded position in the barrel 12, is left partly uncovered. It will, of course, be appreciated that vaginal sponges of different shapes and configurations may be used in conjunction with the applicator 10 of the present invention, provided, of course, that the sponge can be inserted into and delivered from the open upper end 13A of the barrel 12.

Figure 1:
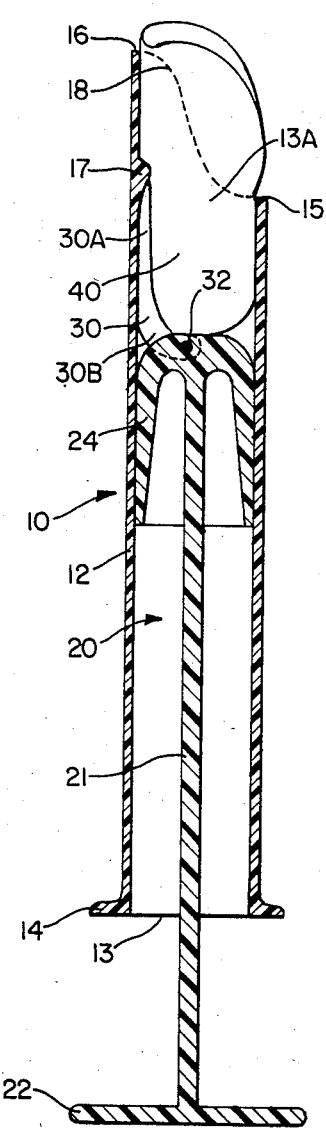
FIG. 1 is a sectional side elevational view of the applicator of the present invention in a loaded position.

An ejector lever 30 is further provided in the applicator 10 and is pivotably connected to the head 24 of the piston 20. The ejector lever 30, which is generally L-shaped with opposed upper and lower legs 30A and 30B, respectively, is pivotably connected along the lower leg 30B thereof to the head 24 of the piston 20 by pivot 32. As shown in FIGS. 1 and 2, as the piston 20 travels upwardly in the barrel 12 with the piston head 24 traveling toward the upper open end 13A, the upper leg 30A of the ejector 30 passes along the inside wall of the barrel 20 until it comes in contact with the curved lower portion of the detent 17. Upon further insertion of the piston 20 into the barrel 12, the upper leg 30A of the ejector 30 is caused to pivot inwardly about pivot 32 and force the sponge 40 out of the barrel 12 against the cervix 50 of the woman. It will be appreciated that the use of the ejector 30 permits the applicator 10 of the present invention to deliver the sponge 40 at an angle relative to the angle of insertion of the barrel 12 into the vagina and, in this manner, apply the sponge 40 directly against the woman's cervix 50. Over-insertion of the piston 20 into the barrel 12 is prevented as the detent 17 acts as a stop when it contacts the head 24 of the piston 20.

It will be appreciated that the applicator 10 of the present invention is adapted to function in the following manner. The sponge 40 is first folded over as shown in FIG. 3 and then introduced or otherwise loaded into the barrel 12 of the applicator 10 through the open upper end 13A thereof. During loading of the sponge 40 into the applicator 10, the piston head 24 is retracted in the direction of lower end 13 by the user grasping the gripping device 22 and pulling it outwardly from the barrel 12. Upon loading of the sponge 40 into the open upper end 13A, the barrel 12 is then inserted into the vagina of the woman with the open upper end 13A positioned relative to the woman's cervix 50. Thumb pressure is then applied against the gripping device 22 at the end of the piston 20 which causes the piston head 24 to move toward the upper open end 13A of the barrel 12. As the piston head 24 moves toward the open upper end 13A, the upper leg 30A of the ejector 30 contacts the detent 17 on the inside wall of the barrel 12 causing the upper leg 30A of the ejector lever 30 to turn inwardly as the lower leg 30B pivots about pivot 32. The upper leg 30A of the ejector lever then forces the sponge 40 out of the end of the barrel 12 and against the cervix 50. The pivoting action of the ejector lever 30 causes the sponge 40 to be delivered at an angle relative to the cervix 50.

After delivery of the sponge 40 against the vaginal cervix 50, the piston head 24 is withdrawn into the barrel 12 and the applicator 10 is removed from the vagina leaving the sponge 40 in place against the cervix 50.

It will be appreciated that the applicator 10 can then be reused with a new sponge after sterilization thereof.

Having thus described the invention with particular reference to the preferred forms thereof, it will be obvious that various changes and modifications may be made therein without departing from the spirit and scope of the invention as defined by the appended claims.

Wherefore, I claim:

1. A reusable applicator adapted to insert a vaginal sponge directly against a woman's cervix, said applicator comprising:
    an outer barrel having an open upper end for receiving and delivering a vaginal sponge directly against a woman's cervix;
    piston means contained within said outer barrel, said piston means including gripping means at one end thereof external of said barrel and a piston head at the opposite end thereof internal within said barrel, said piston head adapted to travel within said barrel toward and away from said open upper end; and
    ejector means pivotably mounted on said piston head, said ejector means adapted to force said vaginal sponge out of said barrel through said open upper end and deliver said sponge directly against a woman's cervix at an angle relative to said applicator as the piston head travels toward the open upper end of the barrel.

2. The applicator of claim 1 wherein said barrel is open at both its opposite upper and lower ends.

3. The applicator of claim 2 wherein a gripping flange is provided about the lower open end of the barrel.

4. The applicator of claim 2 wherein the upper open end of said barrel is tapered from a high point to a low point.

5. The applicator of claim 1 wherein said gripping means comprises a T-shaped handle at the external end of the piston means.

6. The applicator of claim 5 wherein said piston head and said gripping means are interconnected by a piston shaft.

7. The applicator of claim 1 wherein said ejector means comprise an L-shaped ejector lever having upper and lower leg portions.

8. The applicator of claim 7 wherein said ejector lever is pivotably connected to the piston head at a point along the lower leg portion.

9. The applicator of claim 8 wherein a detent is provided on an inside wall of the barrel.

10. The applicator of claim 9 wherein the detent is gradually curved along a side thereof.

11. The applicator of claim 9 wherein the upper leg of the ejector lever is adapted to be pivoted inwardly about said pivot when the ejector lever contacts the detent as the piston head is inserted into the barrel toward the upper open end.

12. The applicator of claim 11 wherein the upper leg of the ejector lever is adapted to contact and deliver the vaginal sponge out of the upper open end of the barrel at an angle relative to the applicator as the piston head travels toward said upper open end.

13. The applicator of claim 1 wherein the vaginal sponge adapted to be inserted is a disc-shaped sponge.

14. The applicator of claim 13 wherein the disc-shaped sponge is first pre-folded prior to insertion into the applicator.

* * * * *